United States Patent [19]

Keblys et al.

[11] Patent Number: 4,929,745

[45] Date of Patent: May 29, 1990

[54] TRANSHALOGENATION OF HALOPHOSPHORUS COMPOUNDS

[75] Inventors: Kestutis A. Keblys; Meng-Sheng Ao; Lester P. J. Burton, all of Baton Rouge, La.

[73] Assignee: Ehtyl Corporation, Richmond, Va.

[21] Appl. No.: 227,231

[22] Filed: Aug. 1, 1988

[51] Int. Cl.$^5$ .............................. C07F 9/14; C07F 9/34; C07F 9/42
[52] U.S. Cl. ....................................................... 558/84
[58] Field of Search .......................... 558/84, 140, 144; 562/808

[56] References Cited

FOREIGN PATENT DOCUMENTS 258611  7/1988  German Democratic Rep. ..................................... 562/808

Primary Examiner—Anton H. Sutto
Attorney, Agent, or Firm—Joseph D. Odenweller

[57] ABSTRACT

Phosphorus compounds having at least one chlorine, bromine or iodine bonded directly to phosphorus are transhalogenated with fluorine by reaction with a hydrogen fluoride salt of a pyridine-type nitrogen base, e.g. pyridine hydrofluoride in an inert solvent.

14 Claims, No Drawings

TRANSHALOGENATION OF HALOPHOSPHORUS COMPOUNDS

BACKGROUND

It is known that fluorine can be exchanged for chlorine, bromine or iodine bonded to phosphorus by reaction of the halophosphorus compound with a metal fluoride. The transhalogenation reaction is quite slow and difficult to push to completion. It is sometimes desirable to replace chlorine, bromine, or iodine bonded to phosphorus with a fluorine atom. For example, L. P. J. Burton U.S. Ser. No. 020,023 filed Feb. 27, 1987 describes a family of hydrocarbyl fluorophosphites that are very effective stabilizers in polyolefins, especially in combination with phenolic antioxidants, and are also hydrolytically stable. These compounds are made by first forming a hydrocarbyl chlorophosphite by reaction of an appropriate aliphatic or aromatic hydroxy compound with $PCl_3$ to form a mono or dichlorophosphite and then transhalogenating the chlorine atom with fluorine by reaction with a metal fluoride such as potassium fluoride.

L. P. J. Burton and M. S. Ao, in U.S. Ser. No. 110,198 filed Oct. 19, 1987, disclose that the transhalogenation of a chlorine, bromine or iodine atom bonded directly to phosphorus by reaction with a fluoride salt can be sharply promoted by including in the reaction mixture a hydrogen halide salt of a pyridine-type compound. While this constitutes an important contribution to the art by decreasing the amount of time required to complete the transhalogenation reaction, a disadvantage of this method is that it employs the use of expensive metal fluoride reactants, such as potassium fluoride.

SUMMARY OF THE INVENTION

It has now been discovered that the transhalogenation of phosphorus compounds having at least one chlorine, bromine or iodine bonded directly to phosphorus with fluorine can be achieved without the use of expensive metal fluorides as fluorinating agents by reacting said phosphorus compound with a hydrogen fluoride salt of a pyridine-type compound in an inert solvent. In most instances, the reaction will go substantially to completion within 1 to 10 hours.

DESCRIPTION OF THE PREFERRED EMBODIMENTS

Thus, a preferred embodiment of the invention is a process for exchanging a halogen bonded to a phosphorus atom with fluorine said process comprising reacting a phosphorus compound having a halogen selected from chlorine, bromine or iodine bonded directly to phosphorus with a hydrogen fluoride salt of a pyridine-type compound in an inert solvent.

The phosphorus-bound halogen that is exchanged with fluorine can be chlorine, bromine or iodine. The exchange is more difficult with chlorine but phosphorus-bound chlorine compounds are the most readily available. Accordingly, the preferred phosphorus-bound halogen is chlorine.

The process can be conducted in a number of inert solvents. Inert solvents include aliphatic hydrocarbons such as hexane, cyclohexane, heptane, isooctane and certain halogenated hydrocarbons such as methylene chloride and the like including mixtures thereof.

The more preferred inert solvents are the aromatic solvents which boil in the range of about 80°–176° C. They include benzene, toluene, xylene and mesitylene including all isomers and all mixtures of isomers and solvents.

The most preferred solvents are toluene and xylene and mixtures thereof.

The amount of solvent used is not critical. A useful amount is about 50–500 parts by weight solvent per 100 parts of phosphorus compound.

The transhalogenation should be conducted at a temperature high enough to cause the halogen exchange to proceed but not so high as to cause undesired degradation of the reaction products. A useful temperature range is about 20°–300° C., more preferably about 50°–200° C. and most preferably at the atmospheric pressure reflux temperature of the reaction mixture. Higher temperatures will of course require a sealed system under pressure.

The reaction time should be long enough to complete the reaction. The reaction is generally complete in about 1–10 hours and in most cases in 5–6 hours.

In the practice of the present invention, the phosphorus-bound halogen compound is reacted with a hydrogen fluoride salt of a pyridine-type compound. Pyridine-type compounds are those compounds that include a pyridine ring in their structure. Examples of these include pyridine, alpha-picoline, beta-picoline, gamma-picoline, quinoline, isoquinoline, 7-methylquinoline, 2,3-dimethylquinoline, lepidine, quinaldine, acridine, quinolinic acid, nicotinic acid, 2-aminopyridine, 2-phenylpyridine and the like including mixtures thereof. The most preferred pyridine-compound is pyridine itself. The most preferred hydrogen fluoride pyridine-type compound is pyridine hydrofluoride.

The amount of hydrogen fluoride pyridine-type reactant used in the process is an amount that causes the transhalogenation to proceed at a rapid rate. A useful range is about 0.5–50 parts by weight per 100 parts of phosphorus compound. A preferred amount is about 1–20 parts and more preferably about 1–15 parts per 100 parts phosphorus compound.

The phosphorus compounds having chlorine, bromine or iodine bonded to phosphorus can have one or two of such halogens bonded to phosphorus. The remaining group or groups bonded to phosphorus are substituted or unsubstituted hydrocarbyl, hydrocarbyloxy or hydrocarbylthio groups. Examples of such halo phosphorus compounds are methyl dichlorophosphite, ethyl dichlorophosphite, butyl dichlorophosphite, dodecyl dichlorothiophosphite, eicosyl dichlorophosphite, triacontyl dichlorophosphite, methyl dibromophosphite, propyl dibromophosphite, tetradecyl diiodophosphite, eicosyl chlorobromophosphite, triacontyl bromoiodophosphite, methyl dichlorophosphate, O-ethyl dichlorothiophosphate, decyl dichlorophosphate, eicosyl dichlorophosphate, O-triacontyl dichlorothiophosphate, methyl dibromophosphate, octyl dibromophosphate, octadecyl dibromothiophosphate, triacontyl dibromophosphate, methyl diiodophosphate, hexadecyl diiodophosphate, eicosyl chloroiodophosphate, O-methyl dichlorothiophosphate, O-decyl dibromothiophosphate, eicosyl diiododithiophosphite, triacontyl dichlorothiophosphonate, phenyl dichlorophosphite, phenyl dibromophosphite, phenyl diiodophosphite, benzyl dichlorophosphite, benzyl dibromophosphite, methyldichlorophosphine, butyldichlorophosphine, dodecyldichlorophosphine, eicosyldibromophosphine, triacontyldiiodophosphine, cyclohexyl dichlorophosphite, cyclohexyl dibromophosphite, cyclohexyl dichlorothiophosphite, cyclohexyl dibromodithiophosphate, dimethyl chlorophosphite, didodecyl chlorophosphite, dieicosyl bromophosphite, ditriacontyl iodophosphite, dimethylchlorophosphine, didodecylbromophosphine, dimethyl chlorothiophosphite, dieicosyl bromodithiophosphite, dimethyl chlorophosphate, didodecyl bromophosphate, dieicosyl bromophosphate, diphenyl chlorophosphite, diphenyl bromophosphite, diphenyl chlorophosphate, diphenyl bromotrithiophosphate, diphenyl chlorophosphate, dibenzyl chlorophosphate, dibenzyl bromophosphite, diphenyl chlorotrithiophosphate, dicyclohexyl chlorophosphate, phenyldichlorophosphine, diphenylbromophosphine, dibenzylchlorophosphine, dimethylchlorophosphine, didodecylbromophosphine, methyleicosyliodophosphine, benzyldibromophosphine and the like.

The preferred phosphorus compounds have the structure

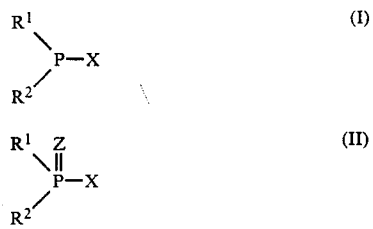

wherein X is chlorine, bromine or iodine, Z is oxygen or sulphur, $R^1$ is selected from the group consisting of substituted and unsubstituted alkoxy, thioalkoxy, aryloxy, thioaryloxy, cycloalkoxy, alkenoxy, and arylalkoxy and $R^2$ is selected from the same group as $R^1$ or is X or $R^1$ and $R^2$ can jointly form a substituted or unsubstituted divalent hydrocarbon group bonded at each end through oxygen or sulphur to the phosphorus atom in structure I or II. More preferably $R^2$ is not X.

Examples of the preferred starting phosphorus compounds are dimethyl chlorophosphite, diethyl chlorophosphite, diethyl bromophosphite, dibutyl iodophosphite, dioctyl chlorophosphite, didodecyl bromophosphite, dieicosyl iodophosphite, triacontyl dichlorophosphite, butyl dibromophosphite, methyl dodecyl chlorophosphite, eicosyl dichlorophosphite, triacontyl dibromophosphite, dimethyl chlorothiophosphite, dodecyl dibromothiophosphite, dioctadecyl chlorothiophosphite, phenyl dichlorophosphite, diphenyl bromophosphite, di(4-tert-butylphenyl) chlorophosphite, di(2,4-di-tert-butylphenyl) bromophosphite, 2-isopropyl-4-methylphenyl dichlorophosphite, di(4-tert-hexylphenyl) chlorophosphite, diphenyl chlorothiophosphite, phenyl dibromothiophosphite, 1-naphthyl dichlorophosphite, dioyclohexyl chlorophosphite, dicyclooctyl bromophosphite, cyclododecyl dichlorophosphite, dicyclohexyl bromothiophosphite, diallyl iodophosphite, di- (but-2-enyl) chlorophosphite, benzyl dichlorophosphite, dibenzyl bromophosphite, di(alpha-methylbenzyl) chlorophosphite, ethyleneglycol chlorophosphite, 2,2'-methylenebis(4,6-di-tertbutylphenyl) chlorophosphite, 2,2'-methylenebis(4-methyl6-tert-butylphenyl) bromophosphite, 2,2'-bis(4,6-di-tert-butylphenyl) chlorophosphite, 2,2'-bis(4,6-di-tert-butylphenyl) chlorophosphate, 2,2'-ethylidenebis(4,6-di-tert-butylphenyl) chlorophosphite, 2,2'-ethylidenebis(4,6-di-tert-butylphenyl) chlorophosphate, di(2,4-di-tert-butylphenyl) chlorophosphate, di(2,6-di-tert-butylphenyl) chlorophosphite, 2,4-di-tert-butylphenyl dichlorodithiophosphate, di[4-(octadecyloxycarbonylethyl)-2,6-tert-butylphenyl]chlorophosphite and the like.

In the more preferred phosphorus compounds $R^1$ and $R^2$ jointly form a divalent hydrocarbon group having the structure

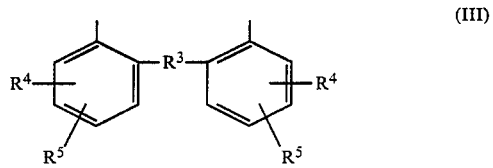

wherein $R^3$ is a methylene or alkylidene bridge or is absent forming a direct ortho-ortho bond between the benzene rings, $R^4$ and $R^5$ are independently selected from alkyl groups, cycloalkyl groups and aralkyl groups and the unsubstituted bond on each benzene ring is bonded through oxygen to said phosphorus atom in structures I or II.

Examples of phosphorus compounds which contain the above divalent hydrocarbon group are 2,2'-methylenebis(4-methyl-6-tertbutylphenyl) chlorophosphite, 2,2'-methylenebis(4-methyl-6-tertbutylphenyl) chlorophosphate, 2,2'-methylenebis(4,6-di-tert-butylphenyl) bromophosphite, 2,2'-ethylidenebis(4-methyl-6-tert-butylphenyl) chlorophosphite, 2,2'-ethylidenebis(4-methyl-6-tert-butylphenyl) chlorophosphate, 2,2'-isopropylidenebis(4-methyl-6-tertpentylphenyl) bromophosphite, 2,2'-butylidenebis(4,6-di-tert-butylphenyl) chlorophosphite, 2,2'-bis(4-sec-dodecyl-6-tert-butylphenyl) chlorophosphate, 2,2'-bis(4-methyl-6-tert-hexylphenyl) bromophosphite, 2,2'-bis(4-methyl-6-cyclohexylphenyl) chlorophosphate, 2,2'-ethylidenebis(4,6-dicyclohexylphenyl) chlorophosphite, 2,2'-methylenebis[4,6-di(alpha-methylbenzyl)-phenyl]bromothiophosphite, 2,2'-ethylidenebis(4-methyl-6(alpha-methylbenzyl)phenyl) chlorophosphite, 2,2'-bis[4,6-di(alpha-methylbenzyl)phenyl]bromophosphite and the like.

In a highly preferred embodiment the $R^4$ groups are bonded at the 6,6'-positions and the $R^5$ groups are bonded at the 4,4'-positions in structure III. Still more preferably both $R^4$ groups are tert-alkyls having 4–12 carbon atoms and $R^5$ is $C_{1-12}$ alkyl, especially a tert-alkyl of 4–12 carbon atoms.

The most preferred phosphorus compound used as a starting material is 2,2'-ethylidenebis(4,6-di-tert-butylphenyl) chlorophosphite.

The following examples show how the reaction is conducted.

EXAMPLE 1

The 2,2'-ethylidenebis(4,6-di-tert-butylphenyl) chlorophosphite starting material was made by heating a mixture of 1300 grams of 2,2'-ethylidenebis(4,6-di-tert-butylphenol), 2 liters of xylene and 13 grams of pyridine in a reaction vessel to 100° C. while maintaining a nitrogen sweep over the reaction surface to assist in HCl removal and thereafter slowly adding 500 grams of PCl₃ to the reaction mixture over a period of 45 minutes. The mixture was then stirred and heated to 135° C. Stirring was continued for 1.5 hours at 135° C. under nitrogen and then allowed to cool to 10° C. The resultant solid was collected by filtration and 500 grams of the filter cake (1484 grams total weight) was washed with 500 grams of xylene and dried at about 80° C. under vacuum overnight. Conversion to 2,2′-ethylidenebis(4,6-di-tertbutylphenyl) chlorophosphite was essentially complete. Analysis by GC (gas chromatography) showed 98 area percent 2,2′-ethylidenebis(4,6-di-tert-butylphenyl) chlorophosphite and 2.0 percent 2,2′-ethylenebis(4,6-di-tert-butylphenyl) hydrogenphosphonate.

To 10 grams of this product mixture dissolved in 18 grams of xylene and heated to 90°–95° C., there was added incrementally, under nitrogen, 2.0 grams of pyridine hydrofluoride (0.02 mol HF; 19.7wt. % HF) over a period of approximately 170 minutes.

The product mixture was allowed to cool overnight, reheated to 90°–95° C. the following morning and analyzed by GC. GC showed 92.4 area percent 2,2′-ethylidenebis(4,6-di-tertbutylphenyl) fluorophosphite, 0.6 percent 2,2′-ethylidenebis(4,6-di-tert-butylphenyl) chlorophosphite and 6.7 percent 2,2′-ethylenebis(4,6-di-tert-butylphenyl) hydrogenphosphonate.

EXAMPLE 2

To 9.84 grams of the 2,2′-ethylidenebis(4,6-di-tert-butylphenyl) chlorophosphite starting reactant material obtained as described in Example 1 dissolved in 17.7 grams of xylene and heated to 95° C., there was added incrementally, under nitrogen, 2.38 gram of pyridine hydrofluoride (0.0196 mol HF; 19.8wt. % HF) over a period of approximately 225 minutes. Analysis by GC showed 95.6 area percent fluorophosphite, 0.1 percent chlorophosphite, 3.2 percent hydrogenphosphonate and 1.1 percent 2,2′-ethylidenebis(4,6-di-tert-butylphenol).

We claim:

1. A process for exchanging a halogen bonded to a phosphorus atom with fluorine said process comprising reacting a phosphorus compound, having 1–2 halogen atoms selected from chlorine, bromine or iodine bonded directly to phosphorus, with a hydrogen fluoride salt of a pyridine-type compound in an inert solvent at a temperature in the range of 20°–300° C. which is high enough to cause the halogen exchange to proceed but not so high as to cause degradation of the reaction products.

2. A process of claim 1 wherein said halogen atom is chlorine.

3. A process of claim 2 wherein said pyridine-type compound is pyridine.

4. A process of claim 3 wherein said solvent is an aromatic hydrocarbon having a normal boiling point in the range of 80°–176° C.

5. A process of claim 4 wherein said inert solvent is xylene.

6. A process of claim 1 conducted at 50°–200° C. wherein said phosphorus compound has the structure

or

wherein X is chlorine, bromine or iodine, Z is oxygen or sulfur, $R^1$ is selected from the group consisting of substituted and unsubstituted alkoxy, thioalkoxy, aryloxy, thioaryloxy, cycloalkoxy, alkenoxy, and arylalkoxy and $R^2$ is selected from the same group as $R^1$ or is X, or $R^1$ and $R^2$ can jointly form a substituted or unsubstituted divalent hydrocarbon group bonded at each end through oxygen or sulfur to the phosphorus atom in structures I or II.

7. A process of claim 6 wherein X is chlorine.

8. A process of claim 7 wherein said pyridine-type compound is pyridine.

9. A process of claim 8 wherein said solvent is an aromatic hydrocarbon having a normal boiling point in the range of 80°–176° C.

10. A process of claim 9 wherein said solvent is xylene.

11. A process of claim 7 wherein said hydrocarbon group has the structure

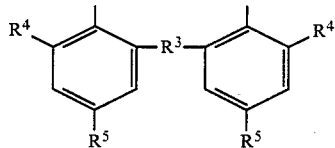

wherein $R^4$ and $R^5$ are alkyl groups.

12. A process of claim 11 wherein $R^4$ and $R^5$ are tert-butyl groups.

13. A process of claim 12 wherein said phosphorus compound has structure I.

14. A process of claim 13 wherein $R^3$ is present and is the ethylidene group.

* * * * *